(12) United States Patent
Owen et al.

(10) Patent No.: US 6,455,531 B1
(45) Date of Patent: Sep. 24, 2002

(54) HYDROXAMIC ACID DERIVATIVES

(75) Inventors: David Alan Owen; Andrew Douglas Baxter; Robert John Watson; Duncan Robert Hannah; John Gary Montana, all of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/806,259

(22) PCT Filed: Dec. 18, 2000

(86) PCT No.: PCT/GB00/04865

§ 371 (c)(1),
(2), (4) Date: Mar. 28, 2001

(87) PCT Pub. No.: WO01/44189

PCT Pub. Date: Jun. 21, 2001

(30) Foreign Application Priority Data

Dec. 17, 2000 (GB) ................................................ 9929979

(51) Int. Cl.⁷ .................. A61K 31/4453; A61K 31/495; C07D 211/32; C07D 295/18
(52) U.S. Cl. ............................ 514/255.01; 514/210.17; 514/319; 514/322; 514/327; 514/330; 514/423; 544/386; 546/198; 546/206; 546/221; 546/226; 546/245; 548/568; 548/953
(58) Field of Search ................................. 546/221, 198, 546/226, 206, 245; 514/327, 321, 330, 319, 210.17, 423, 255.01; 544/386; 548/568, 953

(56) References Cited

U.S. PATENT DOCUMENTS 5,318,964 A * 6/1994 Broadhurst et al. ...... 514/228.2
5,447,929 A * 9/1995 Broadhurst et al. ...... 514/228.2
5,892,112 A   4/1999 Levy et al. .................. 564/133

FOREIGN PATENT DOCUMENTS

| FR | 2597865 | 10/1987 |
| WO | 97/24117 | 7/1997 |
| WO | WO 98/33788 A1 * | 8/1998 |
| WO | WO 99/59568 A1 * | 11/1999 |

\* cited by examiner

*Primary Examiner*—Richard L. Raymond
(74) *Attorney, Agent, or Firm*—Saliwanchik, Lloyd & Saliwanchik

(57) ABSTRACT

Compounds having therapeutic utility are of the formula

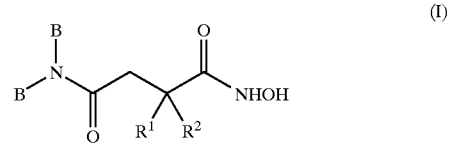

(I)

wherein $NB_2$ is heterocycloalkyl and $R^1$ and $R^2$ are each various substituents or a cyclic group.

21 Claims, No Drawings

HYDROXAMIC ACID DERIVATIVES

This application is a National Stage Application of International Application Number PCT/GB00/04865, filed Dec. 18, 2000 published, pursuant to PCT Article 21(2), in English.

FIELD OF THE INVENTION

This invention relates to hydroxamic acid derivatives, and to their use in medicine.

BACKGROUND OF THE INVENTION

Metalloproteinases, including matrix metalloproteinase (MMP), (human fibroblast) collagenase, gelatinase and TNF convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the adamalysin family (or ADAMs) whose members include TNF convertase (TACE) and ADAM-10, which can cause the release of TNFα from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNF both in vitro and in vivo. See Gearing et al (1994), Nature 370:555–557; McGeehan et al (1994), Nature 370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or TNF are described in WO-A-9513289, WO-A-9611209, WO-A-96035687, WO-A-9603571 1, WO-A-96035712 and WO-A-96035714.

Further, somewhat related compounds are disclosed in U.S. Pat. No. 5,892,112, WO-A-9724117 and FR-A-2597865.

SUMMARY OF THE INVENTION

Compounds according to the invention are of formula (I):

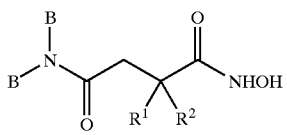

(I)

wherein $R^1$ is a group (optionally substituted with $R^3$) selected from $C_{1-6}$ alkyl, $C_{2-6}$ alkenyl, $C_{2-6}$ alkynyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl; and $R^2$ is H or $C_{1-6}$ alkyl;

or $CR^1R^2$ is cycloalkyl or heterocycloalkyl optionally substituted with $R^3$ or a group (optionally substituted with $R^3$) selected from $C_{1-6}$ alkyl, aryl, $C_{1-6}$ alkyl-aryl, heteroaryl and $C_{1-6}$ alkyl-heteroaryl;

$R^3$ is $OR^7$, $COR^7$, $CO_2R^6$, $CON(R^7)_2$, $N(R^7)_2$, $NR^7COR^7$, $NR^7CON(R^7)_2$, $NR^7CO_2R^8$, $NR^7SO_2R^8$, $S(O)_{0-2}R^8$ and $SO_2N(R^7)_2$; or cycloimidyl (optionally substituted with $R^4$)

$R^4$ is $C_{1-6}$ alkyl;

B—N—B is heterocycloalkyl optionally substituted with $R^5$ or $=NOR^5$;

$R^5$ is H, $R^6$ or a group (optionally substituted with $R^6$) selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl;

$R^6$ is H or a group selected from $N(R^7)_2$ $NR^7COR^7$, $NR^7CON(R^7)_2$, $NR^7CO_2R^8$, $NR^7SO_2R^8$, $OR^7$, $COR^7$, $CO_2R^4$, $CON(R^7)_2$, $S(O)_{0-2}R^8$ and $SO_2N(R^7)_2$;

$R^7$ is H or a group selected from $C_{1-6}$ alkyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl, wherein said group is optionally substituted with $R^8$, $COR^8$, $S(O)_{0-2}R^8$, $CO_2R^8$, $OR^8$, $CONR^4R^8$, $NR^6R^8$ or $SO_2NR^4R^8$, and for each case of $N(R^7)_2$ the $R^7$ groups are the same or different or $N(R^7)_2$ is heterocycloalkyl optionally substituted with $R^8$, $COR^8$, $S(O)_{0-2}R^8$, $CO_2R^8$, $OR^8$, $CONR^4R^8$, $NR^6R^8$ or $SO_2NR^4R^8$; and $R^8$ is $C_{1-6}$ alkyl, aryl, $C_{1-6}$ alkyl-aryl, heteroaryl or $C_{1-6}$ alkyl-heteroaryl;

and the salts, solvates, hydrates, N-oxides, protected amino, protected carboxy and protected hydroxamic acid derivatives thereof.

DESCRIPTION OF THE INVENTION

Preferred compounds of the invention are those wherein $R^1$ is $C_{1-6}$ alkyl or $CR^1R^2$ is heterocycloalkyl.

The compounds of the Examples are particularly preferred.

It will be appreciated that the compounds according to the invention can contain one or more asymmetrically substituted carbon atoms. The presence of one or more of these asymmetric centers in a compound of formula (I) can give rise to stereoisomers, and in each case the invention is to be understood to extend to all such stereoisomers, including enantiomers and diastereomers, and mixtures including racemic mixtures thereof It will further be appreciated that the compounds according to the invention may contain an oxime. This oxime can give rise to geometrical isomers, and in each case the invention is to be understood to extend to all such isomers and mixtures thereof As used in this specification, alone or in combination, the term "$C_{1-6}$alkyl" refers to straight or branched chain alkyl moiety having from one to six carbon atoms, including for example, methyl, ethyl, propyl, isopropyl, butyl, tert-butyl, pentyl, hexyl and the like.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "$C_{2-6}$ alkynyl" refers to a straight or branched chain alkyl moiety having two to six carbon atoms and having in addition one triple bond. This term would include for example, ethynyl, 1-propynyl, 1- and 2-butynyl, 1-methyl-2-butynyl etc.

The term "cycloalkyl" refers to a saturated alicyclic moiety having from three to six carbon atoms and includes for example cyclopropyl, cyclobutyl, cyclopentyl, cyclohexyl and the like. The term "cycloalkenyl" refers to an alicyclic moiety having from three to six carbon atoms and having in addition one double bond. This term includes, for example, cyclopentenyl and cyclohexenyl.

The term "heterocycloalkyl" refers to a saturated heterocyclic moiety having from two to six carbon atoms and one or more heteroatom from the group N, O, S (or oxidised versions thereof) which may be optionally benzofused at any available position. This includes for example azetidinyl, pyrrolidinyl, tetrahydrofuranyl, piperidinyl, benzodioxole and the like. For the group $NB_2$, which is heterocycloalkyl, the saturated heterocyclic moiety must contain at least one N atom. This includes, for example, azetidinyl, pyrrolidinyl, piperidinyl and the like.

The term "heterocycloalkenyl" refers to an alicyclic moiety having from three to six carbon atoms and one or more heteroatoms from the group N, O, S and having in addition one double bond. This term includes, for example, dihydropyranyl.

The term "aryl" refers to an aromatic carbocyclic radical having a single ring or two condensed rings, optionally substituted with an aryl group substituent. This term includes, for example phenyl or naphthyl.

The term "heteroaryl" refers to aromatic ring systems of five to ten atoms of which at least one atom is selected from O, N and S, and optionally substituted with an aryl group substituent. This term includes for example furanyl, thiophenyl, pyridyl, indolyl, quinolyl and the like.

The term "aryl group substituent" refers to a substituent chosen from halogen, CN, $CF_3$, $CHF_2$, $CH_2F$, $OCF_3$, $OCF_2H$, $OCFH_2$ and $NO_2$.

The term "halogen" means fluorine, chlorine, bromine or iodine.

The term "benzofused" refers to the addition of a benzene ring sharing a common bond with the defined ring system.

The term "cycloimidyl" refers to a saturated ring of five to ten atoms containing the atom sequence —C(=O)NC(=O)—. The ring may be optionally benzofused at any available position. Examples include succinimidoyl, phthalimidoyl and hydantoinyl.

The term "optionally substituted" means optionally substituted with one or more of the groups specified, at any available position or positions. The terms "protected amino", "protected carboxy" and "protected hydroxamic acid" mean amino, carboxy and hydroxamic acid groups which can be protected in a manner familiar to those skilled in the art. For example, an amino group can be protected by a benzyloxycarbonyl, tert-butoxycarbonyl, acetyl or like group, or may be in the form of a phthalimido or like group. A carboxyl group can be protected in the form of a readily-cleavable ester such as the methyl, ethyl, benzyl or tert-butyl ester. A hydroxamic acid may be protected as either N or O-substituted derivatives, such as O-benzyl or O-tert-butyldimethylsilyl.

Salts of compounds of formula (I) include pharmaceutically-acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically-labile ester of formula $CO_2R^9$ where $R^9$ may be an ethyl, benzyl, phenethyl, phenylpropyl, "α or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloylmethyl group.

Compounds of the general formula (I) may be prepared by any suitable method known in the art and/or by the following processes. It will be appreciated that, where a particular stereoisomer of formula (I) is required, the synthetic processes described herein may be used with the appropriate homochiral starting material, and/or isomers can be resolved from mixtures using conventional separation techniques (e.g. HPLC). The compounds according to the invention may be prepared by the following process. In the description and formulae below the groups $R^1$, $R^2$ and B are as defined above, and Y is NHOH, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction sequence. Suitable protecting groups for such functionality will be apparent to those skilled in the art. For specific details see Greene T. W. et al, "Protective Groups in Organic Synthesis", Wiley Interscience (1999).

Thus, for example, compounds of the invention may be prepared by the following general route:

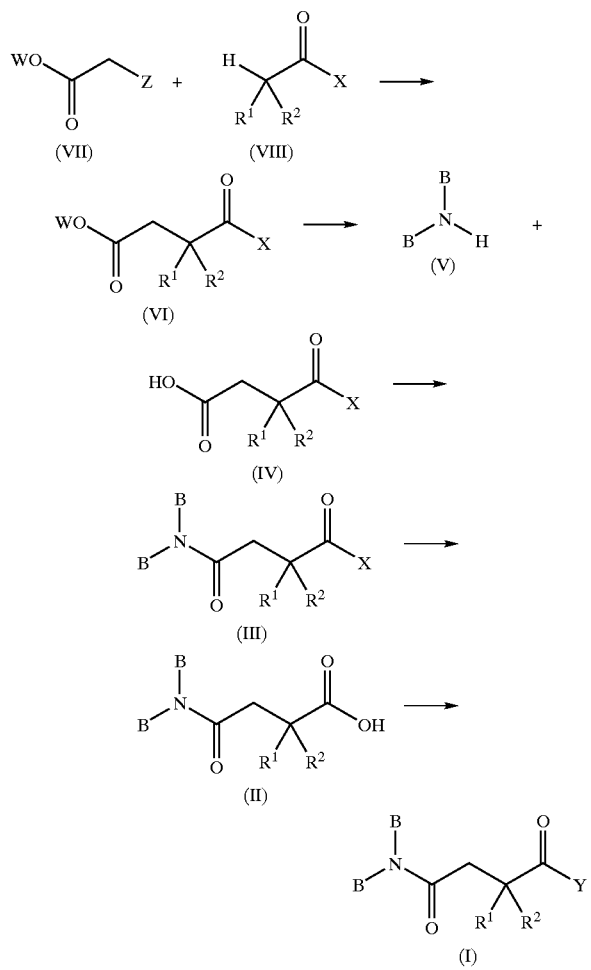

Acids of formula (IV), where X is for example an alkoxy group, e.g. methoxy or ethoxy or a chiral auxiliary, e.g. R-4-benzyl-oxazolidin-2-one, may be prepared by deprotection of an ester of formula (VI) (where W is for example a tert-butyl or benzyl group) using, for example, an acid such as trifluoroacetic acid or by reaction with hydrogen in the presence of an appropriate catalyst such as palladium on carbon. Esters of formula (VI) may be prepared by reaction of an ester of formula (VII), wherein Z is an appropriate leaving group such as a halide, for example a bromide, or an alkyl or aryl sulfonate such as methanesulfonate, with an ester of formula (VIII). Suitable conditions for this reaction include the treatment of compound (VIII) with a strong organic base, such as n-butyllithium or sodium hexamethyldisilazide, in an inert solvent such as tetrahydrofuran at an appropriate temperature such as −78° C. to 0° C., followed by the slow addition of (VII).

Many esters of formulae (VII) and (VIII) or amines of formula (V) are known in the literature or may be prepared by standard methods known to those skilled in the art or by methods described in the examples hereinafter.

The acids of formula (IV) may be used to prepare compounds of formula (III) by reaction with an amine of formula $B_2NH$ (V) using standard methods known to those skilled in the art, for example, by in situ activation of an acid of formula (IV) using for example a diimide such as 1-(3-dimethylaminopropyl)-3-ethylcarbodiimide hydrochloride, advantageously in the presence of catalyst such as 4-dimethylaminopyridine, in a halogenated hydrocarbon, e.g. dichloromethane, followed by subsequent addition of an amine of formula (V). Alternatively, an acid of formula (IV) may be activated, for example by conversion to an acid halide such as an acid chloride by reaction with a halogenating agent such as oxalyl chloride, in the presence of a catalyst such as N,N-dimethylformamide in a halogenated hydrocarbon, e.g. dichloromethane. The acid chloride (which may or may not be isolated) can then be reacted with an amine of formula (V) in the presence of an amine base such as triethylamine in a halogenated hydrocarbon, e.g. dichloromethane.

Carboxylic acids of formula (II) may be prepared by deprotection of a suitably protected carboxylic acid of formula (III), where X is removed for example by lithium hydroxide in the case of an alkyl ester, e.g. ethyl or lithium hydroxide/hydrogen peroxide in the case of a chiral auxiliary such as R-4-benzyl-oxazolidin-2-one, using appropriate solvent and temperature conditions such as those described in the examples hereinafter.

The acids of formula (II) may be used to prepare compounds of formula (I) under conditions well known in the literature. For example, treatment of acids of formula (II) with oxalyl chloride in an inert solvent (such as dichloromethane) gives an intermediate acid chloride, which may or may not be isolated, but which in turn is reacted with hydroxylamine at a suitable temperature such as room temperature to give the desired hydroxamic acids (I). Alternatively, an acid of formula (II) maybe activated in situ using for example a diimide such as 1-(3-dimethylaminopropyl)-3-ethylcarbodiimide hydrochloride, advantageously in the presence of a catalyst such as a N-hydroxy compound, e.g. N-hydroxybenzotriazole, using suitable conditions, e.g. in N,N dimethylformamide at −10° C., prior to the subsequent addition of a suitably protected hydroxylamine such as tert-butyldimethyl silyl hydroxylamine and maybe an an amine base such as N-methylmorpholine followed by warming to ambient temperature. The protecting group maybe removed using appropriate conditions, such as water or tetrabutylammonium fluoride and acetic acid in tetrahydrofuran at 0° C., to yield the desired hydroxamic acids of formula (I).

Compounds of formula (I) may also be prepared by interconversion of other compounds of formula (I). Thus, for example, a compound of formula (I) wherein is a $C_{1-6}$ alkyl group may be prepared by hydrogenation (using palladium on carbon in suitable solvent, such as an alcohol, e.g. ethanol) of a compound of formula (I) wherein $R^1$ is a $C_{2-6}$ alkenyl group.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to the stromelysin, collagenase, gelatinase, ADAM or ADAM-TS enzymes. Compounds according to the invention may also exhibit in vitro inhibition of membrane shedding events known to be mediated by metalloproteinases, for example, α-APP, ACE, TGF-α, TNF-α, Fas ligand, selectins, TNFR-I, TNFR-II, CD30, Il-6R, CD43, CD44, CD16-I, CD16-II, Folate receptor, CD23, or IL-1RII.

The activity and selectivity of the compounds may be determined by use of the appropriate enzyme inhibition test, for example as described in Examples A–M of WO-A-9805635, by the assay for the inhibition of CD23 shedding described in WO-A-9924399 or by the assay of TNF RI shedding described in WO-A-0056704.

This invention also relates to a method of treatment for patients (including man and/or mammalian animals raised in the dairy, meat or fur industries or as pets) suffering from disorders or diseases which can be attributed to metalloproteinases.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment or prophylaxis) of disease or conditions mediated by TNF and/or MMPs in mammals, in particular in humans, which method comprises administering to the mammal an effective amount of a compound of formula (I) above, or a pharmaceutically acceptable salt thereof, and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMs.

The disease or conditions referred to above include inflammatory diseases, autoimmune diseases, cancer, cardiovascular diseases, diseases involving tissue breakdown. Appropriate diseases include rheumatoid arthritis, osteoarthritis, osteoporosis, neurodegeneration, Alzheimer's disease, stroke, vasculitis, Crohn's disease, ulcerative colitis, multiple sclerosis, periodontitis, gingivitis and those involving tissue breakdown such as bone resorption, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, congestive heart failure, endometriosis, atherosclerosis, endosclerosis, aspirin-independent anti-thrombosis, systemic lupus erythematosus and solid organ transplant.

Compounds of formula (I) may also be useful in the treatment of pelvic inflammatory disease (PID), age-related macular degeneration and cancer-induced bone resorption. Further, they can be used in the treatment of lung diseases, e.g. selected from cystic fibrosis, adult respiratory distress syndrome (ARDS), emphysema, bronchitis obliterans-organising pneumonia (BOOP), idiopathic pulmonary fibrosis (PIF), diffuse alveolar damage, pulmonary Langerhan's cell granulamatosis, pulmonary lymphangioleiomyomatosis (LAM) and chronic obstructive pulmonary disease (COPD).

For the treatment of all disorders or diseases previously indicated, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions oft he invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For the purposes of this specification, topical application includes mouth washes and gargles.

Dosage levels of the order of from about 0.05 mg to about 140 mg per kilogram of body weight per day are useful in the treatment of the above—indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day). The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the invention.

INTERMEDIATE 1

2-(2-(4-(4-Chlorobenzoyl)piperidin-1-yl)-2-oxoethyl)-4-methylpentanoic Acid Methyl Ester 4-(4-Chlorobenzoyl)piperidine (0.2 g) was added to a solution of methyl 3-isobutylsuccinic acid (0.15 g) and EDC (0.25 g) in dichloromethane (10 ml) and the solution was stirred for 18 h, then washed with water (10 ml), aqueous citric acid (10 ml), saturated sodium bicarbonate (10 ml) and brine (10 ml), dried over magnesium sulphate (1 g) and evaporated to give the title compound (0.25 g) as a colourless solid.

$R_f$ 0.45 (ether)

INTERMEDIATE 2

2-(2-(4-(4-Chlorobenzoyl)piperidin-1-yl)-2-oxoethyl)-4-methylpentanoic Acid

A solution of Intermediate 1 (0.25 g) in tetrahydrofuran (5 ml) was treated with a solution of lithium hydroxide (0.1 g) in water (5 ml) and the mixture was stirred at room temperature for 24 hours, then evaporated in vacuo, the aqueous residue washed with ether (2×5 ml), acidified with dilute HCl and extracted with ethyl acetate (3×10 ml). The solvent was washed with water (10 ml) and brine (10 ml), dried over magnesium sulphate (1 g) and evaporated to give the title compound (0.18 g) as a colourless solid.

$R_f$ 0.28 (EtOAc)

INTERMEDIATE 3

2-(2-(4-(4-Chlorobenzoyl)piperidin-1-yl)-2-oxoethyl)-4-methylpentanoic acid N-tert-butyldimethylsilyloxyamide A solution of Intermediate 2 (0.18 g) in DCM (10 ml) was treated with EDC (0.15 g) and O-tert-butyldimethylsilylhydroxylamine (0.15 g) and the mixture was stirred for 18 h, then washed with water (10 ml) and brine (10 ml), dried over magnesium sulphate (1 g) and evaporated to give the title compound as a colourless solid (0.12 g).

$R_f$ 0.64 (EtOAc)

INTERMEDIATE 4

4R-Benzyl-3-(3-methylbutyryl)oxazolidin-2-one n-Butyllithium (33.0 ml, 1.6M) was added to a solution of 4R-benzyloxazolidin-2-one (9.0 g) in tetrahydrofuran (100 ml) at −78° C. and the solution was stirred for 30 min, then a solution of isovaleryl chloride (6.1 g) was added dropwise over 20 min. The resulting suspension was stirred for 2 h, then aqueous ammonium chloride (50 ml) was added and the mixture evaporated in vacuo. The product was collected by filtration, washed with water (15 ml) and dried in vacuo to give the title compound (13 g) as a colourless solid.

$R_f$ 0.45 (2:1 ether/hexane)

INTERMEDIATE 5

3S-(4R-Benzyl-2-oxo-oxazolidine-3-carbonyl)-4-methyl-pentanoic Acid tert-Butyl Ester Sodium hexamethyldisilazide (1.0 M in tetrahydrofuran, 23.0 ml) was added to a solution of Intermediate 4 (6.0 g) in tetrahydrofuran at −78 ° C. and the solution was stirred for 30 min, then a solution of tert-butyl bromoacetate (3.7 ml) in tetrahydrofuran was added dropwise. The mixture was stirred for 30 min, then allowed to warm to room temperature and ammonium chloride solution (5 ml) added. The mixture was evaporated in vacuo and the aqueous residue extracted with dichloromethane (3×10 ml). The solvent was washed with water (15 ml), brine (15 ml), dried over magnesium sulphate (5 g) and evaporated to give the title compound (8.6 g) as a colourless solid.

$R_f$ 0.65 (3:2 hexane/ether)

INTERMEDIATE 6

3S-(4R-Benzyl-2-oxo-oxazolidine-3-carbonyl)-4-methyl-pentanoic acid

Trifluoroacetic acid (10 ml) was added to a solution of Intermediate 5 (8.6 g) in dichloromethane (50 ml) and the solution was stirred at room temperature for 2 h, then evaporated in vacuo and the residue azeotroped with heptane to dryness. The residue was dissolved in aqueous sodium bicarbonate (10 ml) and washed with ether (2×10 ml), the aqueous layer acidified with citric acid and extracted with dichloromethane (3×10 ml). The solvent was washed with water (10 ml) and brine (10 ml), dried over magnesium sulphate (5 g) and evaporated to give the title compound as a colourless oil (7.2 g) which crystallised slowly on standing.

$R_f$ 0.45 (ether+1% AcOH)

INTERMEDIATE 7

4-(4-Chlorophenylsulfanyl)piperidine-1-carboylic Acid tert-Butyl Ester

Di-tert-carbonate (9 g) was added to a stirred suspension of 4-bromopiperidine (10 g) in dichloromethane (200 ml). Triethylamine (6.3 ml) was added and the reaction stirred at room temperature for 30 min, before being washed with aqueous citric acid (5%, 100 ml), water (100 ml) and brine (100 ml). The organic layer was dried over magnesium sulphate (5 g), before the solvent was removed in vacuo to yield a colourless oil which was taken up in N,N-dimethylformamide (50 ml). 4-Chlorothiophenol (5.8 g) and potassium carbonate (5.3 g) were added and the reaction heated at 80 ° C. for 6 h. On cooling the reaction was diluted with water (50 ml) and extracted with ether (3×50 ml). The combined organic extracts were washed with water (100 ml), brine (100 ml), dried over magnesium sulphate (2 g), and the solvent removed in vacuo to yield the title compound (14.2 g) as a yellow oil.

$R_f$ 0.43 (2:1 hexane/ether)

INTERMEDIATE 8

4-(4-Chlorobenzenesulfonyl)piperidine-1-carboxylic Acid tert-Butyl Ester

Oxone (25 g) and sodium acetate (9 g) in water (200 ml) were added to a solution of Intermediate 7 (14.2 g) in methanol (300 ml) and the reaction stirred at room temperature for 6 h. The methanol was removed in vacuo and the resulting slurry extracted with dichloromethane (2×100 ml). The combined organic extracts were washed with aqueous sodium hydroxide (2M, 100 ml), water (100 ml), brine (100 ml), dried over magnesium sulphate (3 g) and the solvent removed in vacuo. The oily residue was crystallized from ether/hexane to yield on filtration and drying in vacuo the title compound as a white solid (7.2 g).

$R_f$ 0.29 (ether)

INTERMEDIATE 9

4-(4-Chlorobenzenesulfonyl)piperidine

Trifluoroacetic acid (15 ml) was added to a solution of Intermediate 8 (6.5 g) in dichloromethane (40 ml) and the solution was stirred at room temperature for 3 h, then evaporated in vacuo and the residue azeotroped with heptane to dryness. The residue was dissolved in aqueous sodium bicarbonate (10 ml) and washed with ether (2×10 ml), the aqueous layer acidified with citric acid and extracted with dichloromethane (3×10 ml). The dichloromethane extracts were combined and washed with water (10 ml), brine (10 ml), dried over magnesium sulphate (5 g) and evaporated to give the title compound as a white solid (5.0 g).

$R_f$ 0.25 (EtOAc with 1% ammonium hydroxide)

INTERMEDIATE 10

4(6-Fluorobenzo[d]isoxazol-3-yl)piperidine-1-carboxylic Acid tert-Butyl Ester Di-tert-carbonate (0.9 g) was added to a stirred suspension of (2,4-difluorophenyl)piperidin-4-ylmethanone (1 g) in dichloromethane (30 ml). Triethylamine (0.62 ml) was added and the reaction stirred at room temperature for 2 h, before being washed with aqueous citric acid (5%, 20 ml), water (20 ml) and brine (20 ml). The organic layer was dried over magnesium sulphate (1 g), before the solvent was removed in vacuo to yield a yellow oil which was taken up in ethanol (20 ml). Acetic acid (2 ml) and aqueous hydroxylamine (2 ml) were added and the reaction stirred at room temperature for 2 h. Water (50 ml) was added and the reaction extracted with dichloromethane (3×30 ml). The combined organic extracts were washed with water (50 ml), brine (50 ml), dried over magnesium sulphate (2 g), and the solvent removed in vacuo to yield a yellow oil which was taken up in N,N-dimethylformamide (20 ml) and sodium hydride (0.12 g, 60%) added. The reaction was heated to 80° C. for 3 h, before on cooling being diluted with water (40 ml), and extracted with EtOAc (3×20 ml). The combined organic extracts were washed with water (30 ml), brine (30 ml), dried over magnesium sulphate (1 g) and the solvent removed in vacuo to yield the title compound (0.7 g) as a white solid.

$R_f$ 0.63 (ether)

INTERMEDIATE 11

6-Fluoro-3-piperidin-4-ylbenzo[d]isoxazole

Trifluoroacetic acid (8 ml) was added to a solution of Intermediate 10 (0.7 g) in dichloromethane (20 ml) and the solution was stirred at room temperature for 3 h, then evaporated in vacuo and the residue azeotroped with heptane to dryness. The residue was dissolved in methanol (4 ml), diluted with ether (ca 12 ml) and the solid that formed was collected by filtration. On drying in vacuo, the title compound was yielded as a pink solid (0.65 g).

$R_f$ 0.25 (7% MeOH/dichloromethane with 1% ammonium hydroxide).

INTERMEDIATE 12

4-(Naphthalen-2-yloxy)piperidine-1-carboxylic Acid tert-Butyl Ester

To a stirred solution of 2-naphthol (2.9 g) and 4-hydroxypiperidine-1-carboxylic acid tert-butyl ester (4 g) in tetrahydrofuran (30 ml) at 0° C. was added triphenylphosphine (5.2 g) and diethyl azodicarboxylate (3.2 ml). The reaction was allowed to warm to room temperature and stirred for 16 h. The solvent was removed in vacuo and the slurry taken up in EtOAc (30 ml) and washed with aqueous sodium hydroxide (1M, 2×30 ml), water (30 ml) and brine (30 ml). The organic extract was diluted with hexane (50 ml), and the precipitates were removed by filtration, and the filtrate dried over magnesium sulphate (1 g). The solvent was removed in vacuo to yield the title compound as a white solid (3.4 g).

$R_f$ 0.63 (2:1 ether/hexane).

INTERMEDIATE 13

4-(Naphthalen-2-yloxy)piperidine Hydrochloride

Trifluoroacetic acid (20 ml) was added to a solution of Intermediate 12 (3.4 g) in dichloromethane (60 ml) and the solution was stirred at room temperature for 1 h, then evaporated in vacuo and the residue azeotroped with heptane to dryness. The residue was dissolved in aqueous sodium hydroxide (1M, 10 ml) and washed with ether (2×10 ml), the aqueous layer acidified with citric acid and extracted with dichloromethane (3×10 ml). The solvent was washed with water (10 ml), brine (10 ml), dried over magnesium sulphate (2 g) and evaporated to give a yellow oil. The oil was taken up in methanol (5 ml) and hydrogen chloride in ether (2M, 15 ml) was added. The precipitate was collected by filtration and dried in vacuo to yield the title compound as a white solid (2.6 g).

$R_f$ 0.05 (10% MeOH/dichloromethane)

INTERMEDIATE 14

1-(4R-Benzyl-2-oxo-oxazolidin-3-yl)-4-[4-(4-chlorobenzoyl)-piperidin-1-yl]-2S-isopropylbutane-1,4-dione EDC (0.20 g) was added to a solution of Intermediate 6 (0.32 g) in dichloromethane (20 ml) and the solution was stirred for 30 min, then a solution of 4-(4-chlorobenzoyl) piperidine (0.25 g) was added and the mixture was stirred overnight. The solution was washed with aqueous citric acid (10 ml), aqueous sodium bicarbonate (10 ml) and brine (10 ml), dried over magnesium sulphate (1 g) and evaporated to give the title compound (0.50 g) as a colourless gum.

$R_f$ 0.47 (ether).

Similarly prepared were:

INTERMEDIATE 15

1-(4R-Benzyl-2-oxo-oxazolidin-3-yl)-4-[4-(4-chlorophenoxy)-piperidin-1-yl]-2S-isopropylbutane-1,4-dione From (4R, 3R) 3-(4-benzyl-2-oxo-oxazolidine-3-carbonyl)-4-methylpentanoic acid (0.62 g) and 4-chlorophenoxypiperidine (0.58 g), the title compound was yielded as a colourless solid (1.1 g).

R$_f$ 0.48 (ether)

INTERMEDIATE 16

1-(4R-Benzyl-2-oxo-oxazolidin-3-yl)-4-[4-(4-chlorophenyl)-piperazin-1-yl]-2S-isopropylbutane-1,4-dione From Intermediate 6 (1.7 g) and 4-chlorophenylpiperazine (1.4 g), the title compound was yielded as a colourless foam (2.50 g).

R$_f$ 0.39 (ether)

INTERMEDIATE 17

1-(4R-Benzyl-2-oxo-oxazolidin-3-yl)-4-[4-(4-chlorobenzene-sulfonyl)piperidin-1-yl]-2S-isopropylbutane-1,4-dione From Intermediate 6 (1.02 g) and Intermediate 9 (0.85 g), the title compound was yielded as a white foam (1.46 g).

R$_f$ 0.73 (ether)

INTERMEDIATE 18

1-(4R-Benzyl-2-oxo-oxazolidin-3-yl)-4-[4-(6-fluorobenzo-[d]isoxazol-3-yl)piperidin-1-yl]-2S-isopropylbutane-1,4-dione From Intermediate 6 (0.16 g) and Intermediate 11 (0.18 g), the title compound was yielded as a yellow oil (0.12 g).

R$_f$ 0.45 (2:1 ether/hexane)

INTERMEDIATE 19

1-(4R-Benzyl-2-oxo-oxazolidin-3-yl)-2S-isopropyl-4-[4-(naphthalen-2-yloxy)piperidin-1-yl]butane-1,4-dione From Intermediate 6 (0.31 g) and Intermediate 13 (0.26 g), the title compound was yielded as a yellow oil (0.32 g).

R$_f$ 0.63 (2:1 ether/hexane)

INTERMEDIATE 20

2S-{2-[4-(4-Chlorobenzoyl)piperidin-1-yl]-2-oxoethyl}-3-methylbutyric Acid

Lithium hydroxide (0.15 g) in water (5 ml) was added to a solution of Intermediate 14 (1.8 g) in tetrahydrofuran (20 ml), water (5 Ml) and aqueous hydrogen peroxide (8M, 1.3 ml) at 0° C. and the mixture was stirred for 1 8 h. Sodium sulfite (5 g) in water (10 ml) was added and the mixture was evaporated in vacuo. The aqueous residue was washed with ether (2×10 ml), then acidified with citric acid and extracted with dichloromethane (2×20 ml), the combined dichloromethane extracts were washed with water (30 ml), brine (30 ml), dried over magnesium sulphate (1 g) and evaporated to give the title compound (0.65 g) as a colourless solid.

R$_f$ 0.25 (EtOAc)

Similarly prepared were:

INTERMEDIATE 21

2S-{2-[4-(4-Chlorophenoxy)piperidin-1-yl]-2-oxoethyl}-3-methylbutyric Acid

From Intermediate 15 (1.1 g), to yield the title compound as a colourless solid (0.65g).

R$_f$ 0.40 (EtOAc)

INTERMEDIATE 22

2S-{2-[4-(4-Chlorophenyl)piperazin-1-yl]-2-oxoethyl}-3-methylbutyric Acid

From Intermediate 16 (2.50 g) as a colourless solid (0.80 g).

R$_f$ 0.20 (ether+1% AcOH)

INTERMEDIATE 23

2S-{2-[4-(4-Chlorobenzenesulfonyl)piperidin-1-yl]-2-oxoethyl}-3-methylbutyric Acid From Intermediate 17 (1.46 g), to yield the title compound as a white solid (0.6 g).

R$_f$ 0.43 (EtOAc)

INTERMEDIATE 24

2S-{2-[4-(6-Fluorobenzo[d]isoxazol-3-yl)piperidin-1-yI]-2-oxoethyl}-3-methylbutyric Acid From Intermediate 18 (112 mg), to yield the title compound as a white solid (0.6 g).

R$_f$ 0.25 (ether)

INTERMEDIATE 25

2S-3-Methyl-2-{2-[4-(naphthalen-2-yloxy)piperidin-1-yl]-2-oxoethyl}butyric Acid

From Intermediate 19 (0.32 g), to yield the title compound as a beige oil (0.12 g).

R$_f$ 0.35 (2:1 EtOAc/hexane)

EXAMPLE 1

2S-{2-[4-(4-Chlorobenzoyl)piperidin-1-yl]-2-oxoethyl}-4-methylpentanoic Acid N-hydroxy Amide A solution of Intermediate 3 (0.12 g) was stirred in DCM (10 ml) and a solution of HCl in ether (2 ml) was added dropwise. The mixture was stirred for 10 min, then diluted with hexane (10 ml) and the product isolated by filtration to give the title compound as colourless solid.

R$_f$ 0.35 (10% MeOH/CH$_2$Cl$_2$).

MS 379, 381 (M+1)

EXAMPLE 2

2S-{2-[4-(4-Chlorobenzoyl)piperidin-1-yl]-2-oxoethyl}-3-methylbutyric Acid N-hydroxy Amide EDC (0.20 g) and N-hydroxybenzotriazole (0.15 g) were added to a solution of Intermediate 20 (250 mg) in DMF (10 ml) at −10° C. and the mixture was stirred for 30 min, then a solution of tert-butyldimethyl silyl hydroxylamine (120 mg) and N-methylmorpholine (200 µl) was added. The mixture stirred for 48 h, then added to water (10 ml) and extracted with EtOAc (2×10 ml). The solvent was washed with water (10 ml), aqueous sodium bicarbonate (10 ml), brine (10 ml), dried over magnesium sulphate (1 g) and evaporated and the residue purified by chromatography (6% MeOH/DCM) to give the title compound (120 mg) as colourless solid.

$R_f$ 0.42 (6% MeOH/CH$_2$Cl$_2$);

MS 380 (M$^+$).

Similarly prepared were:

EXAMPLE 3

2S-{2-[4-(4-Chlorophenoxy)piperidin-1-yl]-2-oxoethyl}-3-methylbutyric Acid N-hydroxy Amide From Intermediate 21 (93 mg), to yield the title compound as a colourless solid (30 mg).

$R_f$ 0.37 (10% MeOH/CH$_2$Cl$_2$);

MS 368 (M$^+$).

EXAMPLE 4

2S-{2-[4-(4-Chlorophenyl)piperazin-1-yl]-2-oxoethyl}-3-methylbutyric Acid N-hydroxy Amide From Intermediate 22 (0.80 g), to yield the title compound as a beige foam (0.43 g).

$R_f$ 0.37 (6% MeOH/CH$_2$Cl$_2$);

MS 353 (M$^+$).

EXAMPLE 5

2S-{2-[4-(4-Chlorobenzenesulfonyl)piperidin-1-yl]-2-oxoethyl}-3-methylbutyric Acid N-hydroxy Amide From Intermediate 23 (0.80 g), followed by purification by flash chromatography on silica (eluent 6% MeOH/CH$_2$Cl$_2$) to yield the title compound as a white solid (0.20 g).

$R_f$ 0.29 (6% MeOH/CH$_2$Cl$_2$);

MS 417 (M$^+$).

EXAMPLE 6

2S-{2-[4-(6-Fluorobenzo[d]isoxazol-3-yl)piperidin-1-yl]-2-oxoethyl}-3-methylbutyric Acid N-hydroxy Amide From Intermediate 24 (0.70 g), followed by purification by flash chromatography on silica (eluent 6 % MeOH/CH$_2$Cl$_2$) to yield the title compound as a white solid (0.43 g).

$R_f$ 0.33 (5% MeOH/CH$_2$Cl$_2$);

MS 380 (M+1).

EXAMPLE 7

2S-N-Hydroxy-3-methyl-2-{2-[4-(naphthalen-2-yloxy)-piperidin-1-yl]-2-oxo-ethyl}butyramide From Intermediate 25 (0.10 g), followed by purification by flash chromatography on silica (eluent 10% MeOH/CH$_2$Cl$_2$) to yield the title compound as a white solid (0.035 g).

$R_f$ 0.37 (10% MeOH/CH$_2$Cl$_2$);

MS 385(M+1).

What is claimed is:

1. A compound of formula (I)

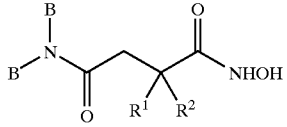

wherein $R^1$ is a moiety (optionally substituted with $R^3$) selected from the group consisting of $C_{1-6}$ alkyl, $C_{2-6}$ alkenyl, $C_{2-6}$ alkynyl, aryl, $C_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl; and $R^2$ is H or $C_{1-6}$ alkyl;

or $CR^1R^2$ is cycloalkyl or heterocycloalkyl optionally substituted with $R^3$ or a moiety, optionally substituted with $R^3$, selected from the group consisting of $C_{1-6}$ alkyl, aryl, $C_{1-6}$ alkyl-aryl, heteroaryl and $C_{1-6}$ alkyl-heteroaryl;

$R^3$ is $OR^7$, $COR^7$, $CO_2R^6$, $CON(R^7)_2$, $N(R^7)_2$, $NR^7COR^7$, $NR^7CON(R^7)_2$, $NR^7CO_2R^8$, $NR^7SO_2R^8$, $S(O)_{0-2}R^8$ and $SO_2N(R^7)_2$; or cycloimidyl (optionally substituted with $R^4$);

$R^4$ is $C_{1-6}$ alkyl;

B—N—B is heterocycloalkyl optionally substituted with $R^5$ or $=NOR^5$;

$R^5$ is H, $R^6$ or a moiety selected from the group consisting of $C_{1-6}$ alkyl, aryl, $C_{1-6}$ alkyl-aryl, heteroaryl, $C_{1-6}$ alkyl-heteroaryl, cycloalkyl, $C_{1-6}$ alkyltycloalkyl, heterocycloalkyl and $C_{1-6}$ alkyl-heterocycloalkyl, wherein said moiety is, optionally, substituted with $R^6$;

$R^6$ is H or a moiety selected from the group consisting of $N(R^7)_2$, $NR^7COR^7$, $NR^7CON(R^7)_2$, $NR^7CO_2R^8$, $NR^7SO_2R^8$, $OR^7$, $COR^7$, $CO_2R^4$ $CON(R^7)_2$, $S(O)_{0-2}R^8$ AND $SO_2N(R^7)_2$;

$R^7$ is H or a moiety selected from the group consisting of $C_{14}$ alkyl, aryl, $C_{1-6}$ alkyl, $c_{1-6}$ alkyl-aryl, heteroaryl, $C_{1-6}$ alkyl-heteroaryl, cycloalkyl, $C_{1-6}$ alkyl-cycloalkyl, heterocycloalkyl and $C_{1-6}$ alkyl-heterocycloalkyl, wherein said moiety is optionally substituted with $R^8$, $COR^8$, $S(O)_{0-2}R^8$, $CO_2R^8$, $OR^8$, $CONR^4R^8$, $NR^6R^8$ or $SO_2NR^4R^8$, and for each case of $N(R^7)_2$ the $R^7$ groups are the same or different or $N(R^7)_2$ is heterocycloalkyl optionally substituted with $R^8$, $COR^8$, $S(O)_{0-2}R^8$, $CO_2R^8$, $OR^8$, $CONR^4R^8$, $NR^6R^8$ or $SO_2NR^4R^8$; and are the same or different or $N(R^7)_2$ is heterocycloalkyl optionally substituted with $R^8$, $COR^8$, $S(O)_{0-2}R^8$, $CO_2R^8$, $OR^8$, $CONR^4R^8$, $NR^6R^8$ or $SO_2NR^4R^8$; and $R^8$ is $C_{1-6}$ alkyl, aryl, $C_{1-6}$ alkyl-aryl, heteroaryl or $C_{1-6}$alkyl-heteroaryl;

or a salt, hydrate, N-oxide, protected amino, protected carboxy or protected hydroxamic acid derivative thereof.

2. A compound of claim 1, wherein $R^1$ is $C_{1-6}$ alkyl.

3. A compound of claim 1, wherein $R^2$ is H.

4. A compound of claim 1, wherein $CR^1R^2$ is optionally substituted cycloalkyl or heterocycloalkyl.

5. A compound of claim 1 which is in the form of a single enantiomer or diastereomer.

6. A compound of claim 1, which is selected from the group consisting of:

a. 2S-{2-[4-(4-chlorobenzoyl)piperidin-1-yl]-2-oxoethyl}-4-methylpentanoic acid N-hydroxy amide, b. 2S-{2-[4-(4-chlorobenzoyl)piperidin-1-yl]-2-oxoethyl}-3-methylbutyric acid N-hydroxy amide, and
c. 2S-{2-[4-(4-chlorophenoxy)piperidin-1-yl]-2-oxoethyl}-3-methylbutyric acid N-hydroxy amide,
d. 2S-{2-[4-(4-chlorophenyl)piperazin-1 -yl]-2-oxoethyl}-3-methylbutyric acid-N-hydroxy amide.

7. A compound of claim 1, selected from

2S-{2-[4-(4-chlorobenzenesulfonyl)piperidin-1-yl]-2-oxoethyl}-3-methylbutyric acid N-hydroxy amide, 2S-{2-[4-(6-fluorobenzo[d]isoxazol-3-yl)piperidin-1-yl]-2-oxoethyl}-3-methylbutyric acid N-hydroxy amide, and 2S-N-hydroxy-3-methyl-2-{2-[4-(naphthalen-2-yloxy)-piperidin-1-yl]-2-oxo-ethyl}butyramide.

8. A compound of claim 2, wherein $R^2$ is H.

9. A pharmaceutical composition comprising a compound according to claim 1 and a pharmaceutically-acceptable diluent or carrier.

10. A method of treating metalloprotease associated disorders or diseases in an individual comprising the administration of therapeutically effective amount of a composition comprising a compound according to claim 1 and a pharmaceutically acceptable carrier to said individual;

wherein said individual suffers from metalloprotease associated disorders or diseases.

11. The method of claim 10, wherein said condition is selected from the group consisting of cancer, asthma, inflammation, inflammatory conditions, autoimmune disease, infectious disease, ocular disease, and age-related macular degeneration.

12. The method of claim 10, wherein said compound is selected from the group consisting of:

a. 2S-{2-[4-(4-chlorobenzoyl)piperidin-1-yl]-2-oxoethyl}-4-methylpentanoic acid N-hydroxy amide,
b. 2S-{2-[4-(4-chlorobenzoyl)piperidin-1-yl]-2-oxoethyl}-3-methylbutyric acid N-hydroxy amide, and
c. 2S-{2-[4-(4-chlorophenoxy)piperidin-1-yl]-2-oxoethyl}-3-methylbutyric acid-N-hydroxy amide,
d. 2S-{2-[4-(4-chlorophenyl)piperazin-1 -yl]-2-oxoethyl}-3-methylbutyric acid-N-hydroxy amide.

13. The method of claim 11, wherein said compound is selected from the group consisting of:

a. 2S-{2-[4-(4-chlorobenzenesulfonyl)piperidin-1-yl]-2-oxoethyl}-3-methylbutyric acid N-hydroxy amide,
b. 2S-{2-[4-(6-fluorobenzo[d]isoxazol-3-yl)piperidin-1-yl]-2-oxoethyl}-3-methylbutyric acid N-hydroxy amide, and
c. 2S-N-hydroxy-3-methyl-2-{2-[4-(naphthalen-2-yloxy)-piperidin-1-yl]-2-oxoethyl}butyramide.

14. The method of claim 10, wherein said compound is in the form of a single enantiomer or diastereomer.

15. The method of claim 10, wherein said compound is 2S-{2-[4-(4-chlorobenzoyl)piperidin-1-yl]-2-oxoethyl}-4-methylpentanoic acid N-hydroxy amide.

16. The method of claim 10, wherein said compound is 2S-{2-[4-(4-chlorobenzoyl)piperidin-1-yl]-2-oxoethyl}-3-methylbutyric acid N-hydroxy amide.

17. The method of claim 10, wherein said compound is 2S-{2-[4-(4-chlorophenoxy)piperidin-1-yl]-2-oxoethyl}-3-methylbutyric acid N-hydroxy amide.

18. The method of claim 10,, wherein said compound is 2S-{2-[4-(4-chlorophenyl)piperazin-1-yl]-2-oxoeythyl}-3-methylbutyric acid N-hydroxy amide.

19. The method of claim 10, wherein said compound is 2S-{2-[4-(4-chlorobenzenesulfonyl)piperidin-1-yl]-2-oxoethyl}-3-methylbutyric acid N-hydroxy amide.

20. The method of claim 10, wherein said compound is 2S-{2-[4-(6-fluorobenzo[d]isoxazol-3-yl)piperidin-1-yl]-2-oxoethyl}-3-methylbutyric acid N-hydroxy amide.

21. The method of claim 10, wherein said compound is 2S-N-hydroxy-3-methyl-2-{2-[4-(naphthalen-2-yloxy)-piperidin-1-yl]-2-oxoethyl}butyramide.

* * * * *

UNITED STATES PATENT AND TRADEMARK OFFICE
CERTIFICATE OF CORRECTION

PATENT NO. : 6,455,531 B1
DATED : September 24, 2002
INVENTOR(S) : David Alan Owen et al.

It is certified that error appears in the above-identified patent and that said Letters Patent is hereby corrected as shown below:

Column 16,
Line 32, "$C_{1-6}$ alkyltycloalkyl," should read -- $C_{1-6}$ alkyl-cycloalkyl, --.
Line 37, $CO_2R^4$ $CON(R^7)_2$," should read -- $CO_2R^4$, $CON(R^7)_2$, --.
Line 38, "AND $SO_2N(R^7)_2$;" should read -- and $SO_2N(R^7)_2$; --.
Line 40, "$C_{14}$ alkyl, aryl, $C_{1-6}$ alkyl, $C_{1-6}$ alkyl-aryl," should read -- $C_{1-6}$ alkyl, aryl, $C_{1-6}$ alkyl-aryl, --.

Column 17,
Line 1, "cblorobenzoyl" should read -- chlorobenzoyl --.
Line 5, "piperazin-1 -yl" should read -- piperazin-1-yl --.
Line 7, "from" should read -- from the group consisting of: --.
Line 8, "2S-{" should read -- a. 2S-{ --.
Line 10, "2S-{" should read -- b. 2S-{ --.
Line 14, "2S-N" should read -- c. 2S-N --.
Line 15, "2-oxo-ethyl" should read -- 2-oxoethyl --.

Column 18,
Line 2, "acid-N-hydroxy" should read -- acid N-hydroxy --.
Line 3, "piperazin-1 -yl" should read -- piperazin-1-yl --.
Line 24, "claim 10,," should read -- claim 10, --.

Signed and Sealed this

Eighteenth Day of March, 2003

JAMES E. ROGAN
*Director of the United States Patent and Trademark Office*